United States Patent [19]

Zimmer

[11] Patent Number: 4,692,155
[45] Date of Patent: Sep. 8, 1987

[54] CATHETER

[75] Inventor: Gabriele Zimmer, Homburg, Fed. Rep. of Germany

[73] Assignee: pfm, Plastik fur die Medizin GmbH, Cologne, Fed. Rep. of Germany

[21] Appl. No.: 808,280

[22] Filed: Dec. 12, 1985

[30] Foreign Application Priority Data

Dec. 14, 1984 [DE] Fed. Rep. of Germany ....... 3445560

[51] Int. Cl.⁴ .............................................. A61M 5/00
[52] U.S. Cl. .................................... 604/177; 604/283
[58] Field of Search ................... 604/177, 283, 8, 264; 128/DIG. 26; 285/254, 242-244

[56] References Cited

U.S. PATENT DOCUMENTS

| 3,540,451 | 11/1970 | Zeman | 604/8 X |
| 4,341,212 | 7/1982 | Medwid | 604/177 |
| 4,592,749 | 6/1986 | Ebling et al. | 604/283 |

FOREIGN PATENT DOCUMENTS 1494816 12/1977 United Kingdom ................ 604/283

Primary Examiner—Stephen C. Pellegrino
Attorney, Agent, or Firm—Keil & Weinkauf

[57] ABSTRACT

A catheter for drainage purposes that is to be used predominantly in the area of the skull in the case of operations, having a closed distal end, said end area being perforated by holes and having a connecting part (6) arranged at the rear end of the catheter tube (1) and having a wing cannula (2) with double wings inserted into the catheter tube (1) in the proximity of the rear end of the catheter tube (1), the parts of the cut catheter tube (1) pushed onto the ends of the metal cannula (4) of the wing cannula (2) being fixed by means of fixing threads (5) so that the catheter tube (1) is pressed into ring grooves on the exterior side of the metal cannula (4).

7 Claims, 1 Drawing Figure

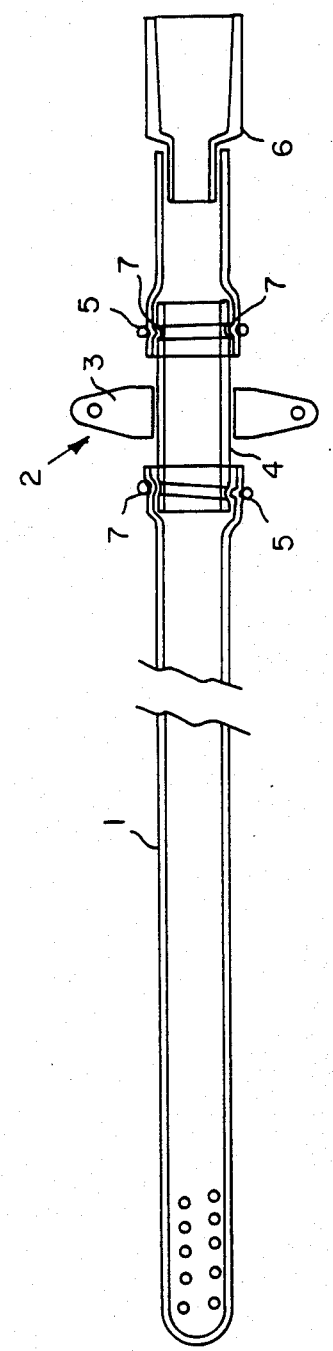

CATHETER

This invention relates to a drainage catheter that is to be used predominantly in the area of the skull in the case of operations.

From DE-OS No. 26 38 832, a device is known for drawing off contrast medium from the vertebral duct of patients, where an oblong cannula is used for the drawing-off that, at its closed distal end, has several lateral openings that are connected with the hollow space of the cannula and at the proximal end of which a connecting piece is provided for the connecting of a tube. The connecting end of the tube, by means of which a detachable connection to the cannula can be established, has two wings extending to the outside in opposite direction that have the purpose of facilitating the fastening at the connecting piece of the cannula.

In U.S. Pat. No. 3,654,932, a drainage catheter is described that is to be used in the area of the skull and the closed distal end of which has several openings arranged laterally next to one another in longitudinal direction. At the proximal end of the actual drainage catheter, a pumping piece is connected that forms the transition to a cannula through which the draining fluid can be introduced into a blood vessel. In order to be able to fix the pumping piece in a predetermined position in the patient, it has two wings projecting out in opposite directions.

Also known as drainage catheters used in operations on the skull are catheters having a thin catheter tube and a perforated point. A connector having a Luer cone may be connected to the usually relatively short catheter tube made of a soft plastic material. Catheters are also known for this purpose in which double wings are pushed onto the catheter tube in order to make possible a fixing of the part of the catheter tube remaining outside the scalp at the scalp.

The known commercially available catheters, however, have the disadvantage that they are relatively short so that in most cases the piece remaining outside the scalp is hardly suitable for a secure fixing and fastening of the wings as well as of the connector. In addition, an adaptation to varying space conditions is not possible so that the catheter end must frequently be fixed in the proximity of the cut scalp.

It is the objective of the invention to provide a catheter of the initially mentioned type that can be easily adapted to special space conditions and is safer to handle than the known embodiments.

This objective is achieved by a catheter having a closed distal end that in the end area has a perforation and having a connecting part arranged at the rear end and double wings in the proximity of the rear end. The characterizing part of the embodiment according to the invention consists of the fact that in the proximity of the rear end of the catheter tube, a wing cannula having double wings is inserted into said catheter tube and the parts of the cut catheter tube that are pushed onto the ends of the metal cannula of the wing cannula are fixed by means of fixing threads, the catheter tube being pressed into ring grooves on the exterior side of the metal cannula.

Preferred embodiments are described in the subclaims.

It is especially advantageous when the inside diameter of the metal cannula corresponds to the inside diameter of the catheter tube because a constant interior cross-section is advantageous for the discharge of secretion. The elasticity of the relatively soft material of the catheter tube permits the pushing of the tube onto the metal cannula and also results in a tight fit because of the required expansion. On the exterior side of the cannula, on each side of the double wing, at least one ring groove is provided making possible a durable fixing of the pushed-on catheter tube on the metal cannula by means of fixing threads. According to the length of the cannula, two or several ring grooves may also be provided for the fixing of the catheter tube.

At the rear end of the catheter tube, a connecting piece is arranged that is preferably firmly connected with the catheter tube. The firm connection may take place by bonding or gluing. The connecting part has a so-called female Luer cone. Such cones and cone connections for medical instruments are described in DIN 13 090.

The outside diameter of the catheter tube is preferably 2.33–4 mm; especially preferable are about 3 mm. The wall thickness of the catheter tube is 0.4 mm to 0.8 mm. Preferably, the catheter tube is 150 to 350 mm long, larger lengths being preferred, such as about 200 mm or about 300 mm.

For the catheter tube, the conventional soft and elastic, medically well-tolerated plastics are used, such as silicone caoutchouc, medical PVC, polyethylene or a similar material. A perforation is provided at the point of the cathether tube over a length of 10 to 20 mm. An example are rows of holes extending in parallel to one another in longitudinal direction and distributed over the circumference of the catheter tube. However, it is also possible that the holes are arranged differently.

In a preferred embodiment of the invention, the catheter tube is provided with a medium supplying a contrast in the case of x-ray irradiation. In this case, a complete preparation is possible starting at the tip as well as a graduation by means of points, rings or lines arranged at a distance from one another, over a length of up to approximately 100 mm. A constrast strip may also exist that extends along the catheter tube.

A special advantage of the catheter according to the invention is the fact that it can first be brought on the market with a separately wrapped wing cannula, and the cutting of the catheter tube and the inserting of the wing cannula takes placed only immediately before use. The catheter tube in this case is longer than in the case of the known catheters. During the cutting and the inserting of the wing cannula, an adaptation of the length of the catheter tube to the respective application will then easily be possible. The manufacturing and the storage of the catheter may then take place using a uniform length. Catheters are only required that have different tube diameters. In order to be able to better handle and insert the relatively soft and not very stiff catheter tube, a so-called inserting needle is first arranged in the catheter. This needle will be pulled out before the start of the drainage and during the insertion into the wound.

The invention will be explained in detail by means of the figure.

The catheter tube made of a soft elastic plastic material has the reference number 1. The front point is closed and has a perforation with longitudinally extending rows of holes that are distributed over the circumference of the catheter tube 1. At the rear end of the catheter tube 1, a connecting part 6 is fastened having a so-called Luer cone. The figure shows the catheter according to the invention after the catheter tube 1 was cut and the wing cannula 2 was inserted. The two ends of the cut catheter tube 1 are pushed onto the metal cannula 4 and are additionally secured by means of fixing threads 5. On the exterior side, the metal cannula has ring grooves 7 so that the catheter tube by means of the fixing threads 5 is pressed into the ring groove and a firm fit is ensured. At the metal cannula 4 double wings 3 are arranged for the development of the wing cannula 2. These double wings 3 each have a hole in order to be able to connect the wing with the scalp so that a firm fixing of the end of the catheter is possible. The double wings 3 preferably consist of a plastic material and are placed onto the metal cannula 4.

I claim:

1. A two piece cut elastic catheter tube having a closed distal end having perforations and having a connecting part arranged at the rear end and having a metal cannula having a pair of plastic wings secured thereto inserted between the cut catheter tube in the proximity of the rear end of the catheter tube, the parts of the cut catheter being attached onto the metal cannula and fastened by means of fixing threads, the catheter tube being pressed on ring grooves on the exterior side of the metal cannula.

2. A catheter according to claim 1, wherein the inside diameter of the metal cannula corresponds to the inside diameter of the catheter tube.

3. A catheter according to claim 1, wherein the outside diameter of the catheter tube is about 2.33 mm to about 4 mm.

4. A catheter according to claim 1, wherein the rear end of the catheter tube is connected firmly with a connecting part having a female Luer cone.

5. A catheter according to claim 1, wherein the catheter tube has a length of about 150 mm to about 350 mm.

6. A catheter according to claim 1, wherein the catheter tube is provided with an X-ray contrasting means.

7. A catheter according to claim 1, wherein the perforations are distributed over the circumference of the distal end.

* * * * *